United States Patent
Takekoshi

(10) Patent No.: US 7,511,721 B2
(45) Date of Patent: Mar. 31, 2009

(54) RADIOGRAPHIC IMAGE CONNECTION PROCESSING METHOD, RADIOGRAPHIC IMAGE CONNECTION PROCESSING APPARATUS, COMPUTER PROGRAM, AND COMPUTER-READABLE RECORDING MEDIUM

(75) Inventor: Koji Takekoshi, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/929,467

(22) Filed: Aug. 31, 2004

(65) Prior Publication Data

US 2005/0046642 A1    Mar. 3, 2005

(30) Foreign Application Priority Data

Sep. 2, 2003    (JP)    ............................. 2003-310438

(51) Int. Cl.
G09G 5/00    (2006.01)
G06K 9/00    (2006.01)

(52) U.S. Cl. ..................... 345/630; 345/629; 345/632; 345/634; 345/635; 345/636; 382/128; 382/132; 382/284; 382/286

(58) Field of Classification Search ................ 345/619, 345/629, 630, 632, 634, 635, 636; 382/128, 382/132, 284, 286

See application file for complete search history.

(56) References Cited

U.S. PATENT DOCUMENTS

| | | | | |
|---|---|---|---|---|
| 4,258,264 A | | 3/1981 | Kotera et al. ................ 250/484 |
| 4,453,266 A | * | 6/1984 | Bacus ......................... 382/134 |
| 4,686,580 A | * | 8/1987 | Kato et al. .................. 358/451 |
| 4,789,929 A | * | 12/1988 | Nishimura et al. ............ 378/15 |
| 5,111,045 A | | 5/1992 | Konno et al. ............. 250/327.2 |
| 5,222,158 A | * | 6/1993 | Takasaki et al. ............. 382/284 |
| 5,272,760 A | * | 12/1993 | Echerer et al. .............. 382/132 |
| 5,361,767 A | * | 11/1994 | Yukov ........................ 600/442 |
| 5,426,709 A | * | 6/1995 | Yoshida et al. .............. 382/132 |
| 5,426,725 A | * | 6/1995 | Kilgore ...................... 715/515 |
| 5,465,163 A | * | 11/1995 | Yoshihara et al. ........... 358/444 |
| 5,469,536 A | * | 11/1995 | Blank ......................... 345/594 |
| 5,768,439 A | * | 6/1998 | Suzuka et al. ............... 382/254 |
| 6,269,177 B1 | | 7/2001 | Dewaele et al. ............. 382/131 |
| 6,273,606 B1 | | 8/2001 | Dewaele et al. ............. 378/174 |
| 6,304,284 B1 | * | 10/2001 | Dunton et al. ................ 348/36 |
| 6,429,862 B1 | * | 8/2002 | Teramoto .................... 345/419 |
| 6,603,988 B2 | * | 8/2003 | Dowlatshahi ............... 600/407 |
| 6,822,624 B2 | * | 11/2004 | Naimer et al. ................. 345/9 |
| 7,010,751 B2 | * | 3/2006 | Shneiderman .............. 715/232 |

(Continued)

FOREIGN PATENT DOCUMENTS

JP    55-12429 A    1/1980

(Continued)

*Primary Examiner*—Ulka Chauhan
*Assistant Examiner*—Jeffrey J Chow
(74) *Attorney, Agent, or Firm*—Fitzpatrick, Cella, Harper, Scinto

(57) ABSTRACT

In a radiographic image connection processing method of connecting plural partial radiographic images, the partial radiographic images are selected, and if appropriate the operation mode is changed, e.g., from an image position adjustment mode, for adjusting a position of the selected partial radiographic image, to an image measurement mode, for measuring the selected partial radiographic image, or vice versa. The selected partial radiographic images are connected. Thus, it is possible to achieve image position adjustment and image measurement during radiographic image connection, and it is also possible to achieve smooth performance of the operations for image position adjustment and image measurement.

11 Claims, 9 Drawing Sheets

U.S. PATENT DOCUMENTS

| | | | |
|---|---|---|---|
| 2001/0017945 A1* | 8/2001 | Horie | 382/284 |
| 2002/0030683 A1* | 3/2002 | Alexander | 345/440.1 |
| 2002/0048394 A1* | 4/2002 | Nagata et al. | 382/132 |
| 2003/0018245 A1* | 1/2003 | Kaufman et al. | 600/407 |
| 2003/0026469 A1* | 2/2003 | Kreang-Arekul et al. | 382/132 |
| 2004/0193054 A1* | 9/2004 | Leblanc et al. | 600/452 |
| 2005/0001850 A1 | 1/2005 | Tago et al. | 345/619 |
| 2005/0203384 A1* | 9/2005 | Sati et al. | 600/426 |

FOREIGN PATENT DOCUMENTS

| | | |
|---|---|---|
| JP | 63-189853 A | 8/1988 |
| JP | 3-287248 A | 12/1991 |
| JP | 3-287249 A | 12/1991 |
| JP | 11-244269 A | 9/1999 |
| JP | 2000-132667 | 5/2000 |
| JP | 2000-232976 | 8/2000 |
| JP | 2000-342567 A | 12/2000 |
| JP | 2002-94772 | 3/2002 |
| JP | 2002-140688 | 5/2002 |

\* cited by examiner

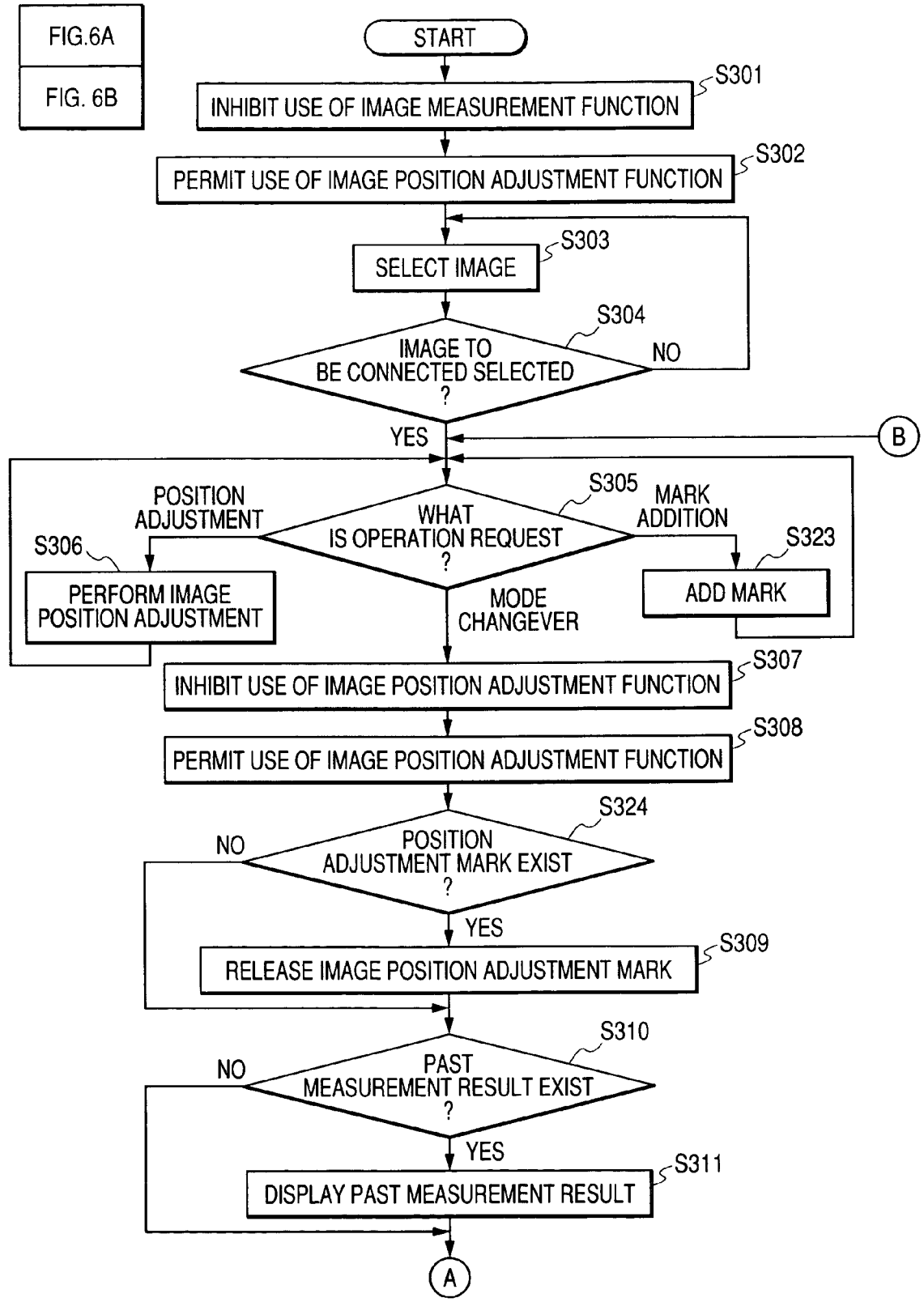

RADIOGRAPHIC IMAGE CONNECTION PROCESSING METHOD, RADIOGRAPHIC IMAGE CONNECTION PROCESSING APPARATUS, COMPUTER PROGRAM, AND COMPUTER-READABLE RECORDING MEDIUM

BACKGROUND OF THE INVENTION

1. Field of the Invention

The present invention relates to a radiographic image connection processing method, a radiographic image connection processing apparatus, a computer program for executing the radiographic image connection processing method, and a computer-readable recording medium storing the computer program for executing the radiographic image connection processing method. In particular, the present invention relates to a technique which is suitable for generating a whole image based on plural partial radiographic images generated from a common subject portion.

2. Related Background Art

Conventionally, a so-called radiographic image diagnosis which obtains an image of a patient by using electromagnetic radiation (X-rays) and thus obtains internal information about the patient is widely executed. Here, in conventional radiography, a film is held together with an intensifying screen in a cassette, a patient is photographed using radiation rays, and the photographed film is developed, whereby a radiographic image of the patient is obtained.

The size of the film to be used at that time is standardized, and the maximum film that is generally and widely used is a so-called half-size film, having the size 14 inches×17 inches.

In a case where so-called lower limb whole-length photographing or whole spine (or backbone) photographing, which aims to measure a bone, is performed, the half-size film of 14 inches×17 inches is too small in size to be used. Thus, in that case, there is used a method in which a so-called long cassette capable of holding a long film is used to photograph a whole-length lower limb or a whole spine and thus obtain the image thereof on the long film. However, even in that case, another method may be adopted because it is hard for an operator to deal with the long film when developing it. In this alternative method, plural half-size films (each 14 inches×17 inches) are held in the long cassette so that the successive films partially overlap each other, and the image obtained by photographing the whole-length lower limb or the whole spine is formed on these films. Further, in this method, the films on which the photographed image has been formed are developed one by one, and then the developed images are appropriately connected with each other using adhesive tape or the like, to obtain the whole image.

On one hand, in recent years, an apparatus which can directly photograph a subject and thus obtain a radiographic image thereof as a digital image has been developed. Japanese Patent Application Laid-Opens Nos. S55-012429 and S63-189853 and the like disclose, e.g., a method in which a photostimulable phosphor detector is used as an apparatus for detecting an amount of radiation irradiated on the subject and then forming as an electrical signal the radiographic image in correspondence with the detected amount of the radiation.

In the apparatus like this, photostimulable phosphor is applied or evaporated on and then fixed to a sheet-like substrate to form the photostimulable phosphor detector, and the radiation transmitted through the subject is irradiated on the formed detector, whereby the irradiated radiation is absorbed by the photostimulable phosphor. Then, the photostimulable phosphor is excited by light or heat energy, the radiation energy stored in the photostimulable phosphor as the result of the above absorption is emitted as fluorescence, and the emitted fluorescence is photoelectrically converted, thereby obtaining the electrical image signal.

In addition, Japanese Patent Application Laid-Open H03-287248 proposes a method of performing, e.g., whole spine photographing by using such an apparatus as above. In this method, more specifically, a long cumulative phosphor sheet which has a recording area corresponding to the length of the whole spine of a subject is used to perform the photographing.

Moreover, Japanese Patent Application Laid-Open No. H11-244269 proposes a method in which plural cassettes respectively holding photostimulable phosphor detectors are arranged partially overlapping each other, the cassettes are held in this arrangement in a special cassette holder, and the subject is photographed.

Japanese Patent Application Laid-Open No. H03-287249 proposes a method in which plural photostimulable phosphor detectors are arranged partially overlapping each other, a subject is photographed to obtain plural partial radiographic images, and then the partial radiographic data corresponding to these images are synthesized to generate a whole image.

On one hand, in recent years, an apparatus which can photograph a subject by using a semiconductor sensor and obtain a radiographic image thereof as a digital image is developed. More specifically, in this type of apparatus, which uses the semiconductor sensor, generally, phosphor is applied or adhered to the semiconductor sensor in advance. Thus, incident radiation is first converted into light by the applied or adhered phosphor, the converted light is detected by the semiconductor sensor, and the detected light is then photoelectrically converted into an electrical signal.

In the apparatus of this type, because the area photographable by the semiconductor sensor is limited or restricted, it is impossible to photograph the whole spine of a subject with one exposure. For this reason, the subject is photographed plural times to obtain plural partial radiographic images, the obtained plural images are displayed, and whole-image data, representing a single whole image, is then generated based on plural sets of partial radiographic image data corresponding to the displayed plural images.

Japanese Patent Application Laid-Open No. 2000-342567 proposes a method of generating whole-image data from plural partial radiographic image data respectively obtained by photographing a subject plural times. According to this method, generally, a user interactively generates the whole image data. More specifically, in a synthesis image generation step to be performed in this method, the radiographic image of the subject (target) is first displayed, the partial radiographic images to be synthesized are appropriately selected from the displayed image, the connection positions at which the successive partial radiographic images should be connected with others are designated respectively on the selected partial radiographic images, and the partial radiographic images are actually connected and synthesized on the basis of the designated connection positions, thereby generating a whole image. As described above, various examples for mutually synthesizing or connecting the plural partial radiographic images are proposed, but none of these examples mention a problem which may occur during in measuring the radiographic image.

In a case where plural radiographic images are connected as above, when position adjustment of the radiographic images and measurement of the radiographic images are simultaneously performed, there is a fear that the position adjustment of the images may shift immediately after the measurement of the images, and, in such a case, the connected and synthesized image is different from the measured result.

Moreover, in a case where a mark used for the position measurement and/or the measured result obtained by the position measurement are displayed on the radiographic images, there is a fear that the mark and/or the result remaining on the display may interfere with the position adjustment of the radiographic images and/or the measurement of the radiographic images, which are the intended purpose.

Furthermore, in a case where a distance extending across the successive radiographic images is measured and then an enlargement ratio of one of these images is changed, there is a fear that the accuracy of the measured result may suffer.

SUMMARY OF THE INVENTION

The present invention is made in consideration of the above conventional problems, and a first object of the present invention is to provide radiographic image connection processing apparatus and method that can perform appropriate image position adjustment and image measurement when plural radiographic images are connected with each other.

A second object of the present invention is to enable a user smoothly to perform an operation for image position adjustment and an operation for image measurement.

In order to achieve the above objects, there is provided a radiographic image connection processing method of connecting plural partial radiographic images, in which the partial radiographic images are selected, and if appropriate the operation mode is changed, e.g., from an image position adjustment mode, for adjusting a position of the selected partial radiographic image, to an image measurement mode, for measuring the selected partial radiographic image, or vice versa. The selected partial radiographic images are connected. Thus, it is possible to achieve image position adjustment and image measurement during radiographic image connection, and it is also possible to achieve smooth performance of the operations for image position adjustment and image measurement.

Other objects and features of the present invention will be apparent from the following description, taken in conjunction with the accompanying drawings.

DETAILED DESCRIPTION OF THE PREFERRED EMBODIMENTS

First Embodiment

Hereinafter, the first embodiment of the present invention will be explained with reference to the attached drawings.

Figure 1:
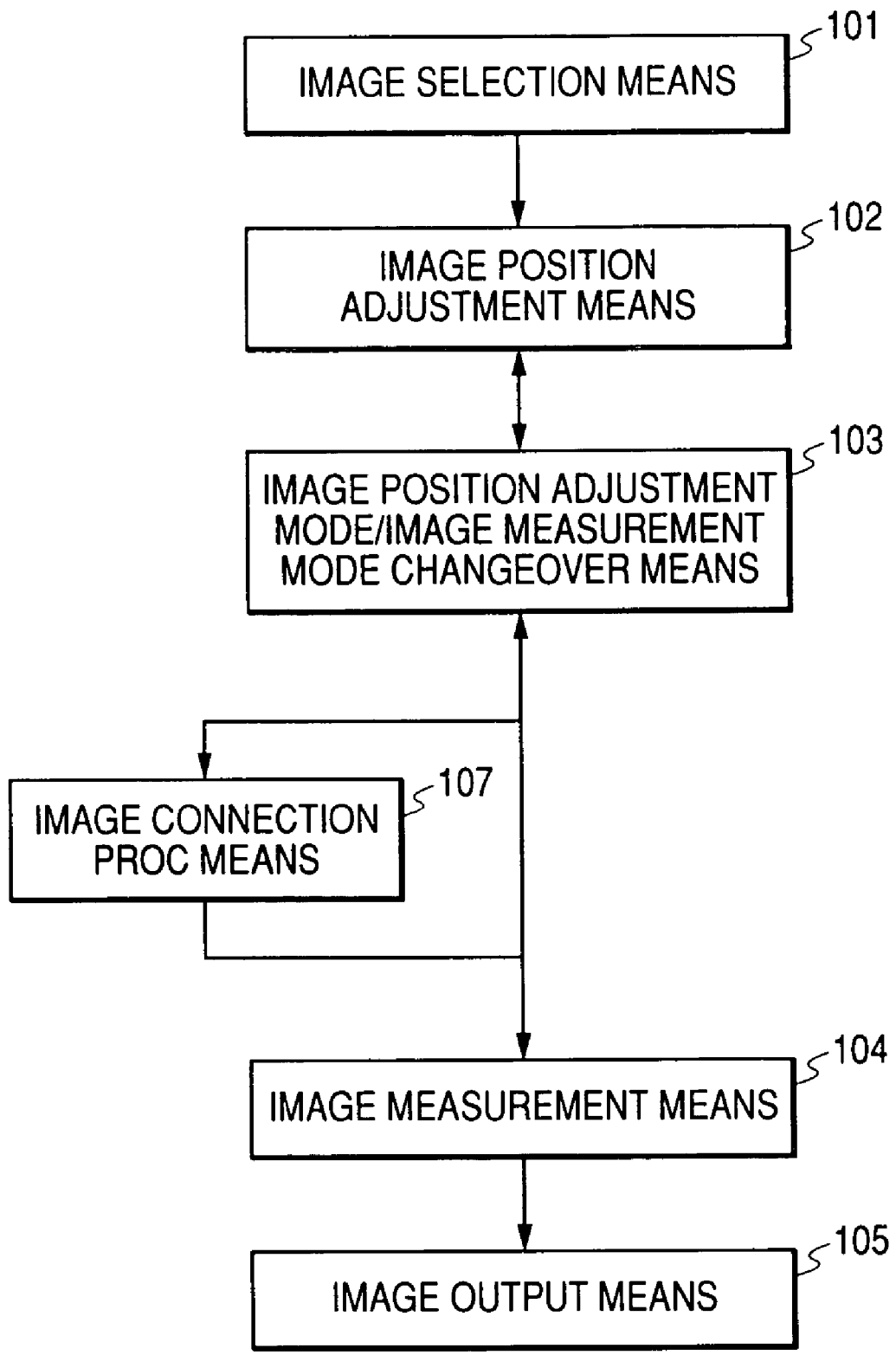
FIG. 1 is a block diagram showing an example of the structure of a radiographic image connection processing apparatus according to the first embodiment of the present invention.

FIG. 1 is a block diagram showing an example of the structure of a radiographic image connection processing apparatus according to the present embodiment. Incidentally, in the following explanation, it should be noted that a radiographic image (partial radiographic image) which is generated by transmitting radiation through a subject is simply referred to as an image as occasion demands. Besides, as a method of generating the radiographic image, for example, there is a method in which the radiographic image is generated by using a digital X-ray imaging apparatus equipped with a flat panel detector. However, in the present embodiment, the method of generating the radiographic image is not specifically limited.

In FIG. 1, numeral 101 denotes an image selection means which selects images to be connected, numeral 102 denotes an image position adjustment means which adjusts the positions of the images to be connected, numeral 103 denotes an image position adjustment mode/image measurement mode changeover means which appropriately changes an image position adjustment mode and an image measurement mode, numeral 104 denotes an image measurement means which measures the image, numeral 105 denotes an image output means which outputs the connected image (that is, the image made by connecting the partial images), and numeral 107 denotes an image connection processing means which performs an image connection process for the selected images.

Next, an example of the operation procedure of the radiographic image connection processing apparatus according to the present embodiment will be explained with reference to the flow chart shown in FIG. 2.

More specifically, a step S201 is an image measurement function use inhibition step. Because the image position adjustment mode is set in a mode initial condition after an image connection screen started, the image position adjustment function is set to be usable and the image measurement function is set to be unusable.

Here, such a usable state is set as, e.g., a button enable state or a button selectable state. However, the present embodiment is not limited to this. That is, any state can be adopted if it is the state enabling to use the function in question. On the other hand, such an unusable state is set as, e.g., a button disable state or a button undisplayed state (the state that a button itself is not displayed). However, the present embodiment is not limited to this.

In the image position adjustment function which is set to be in the usable state, it is possible to perform an image upward shift, an image downward shift, an image rightward shift, an image leftward shift, an image 90° rotation, an image −90° rotation, an image free rotation, an image up-and-down inversion, an image front-and-back reversal, an image cutout, a window width change, a window level change, and the like. (Here, it should be noted that the image cutout is an operation for eliminating the portion unnecessary to connect the selected images.)

Figure 3:
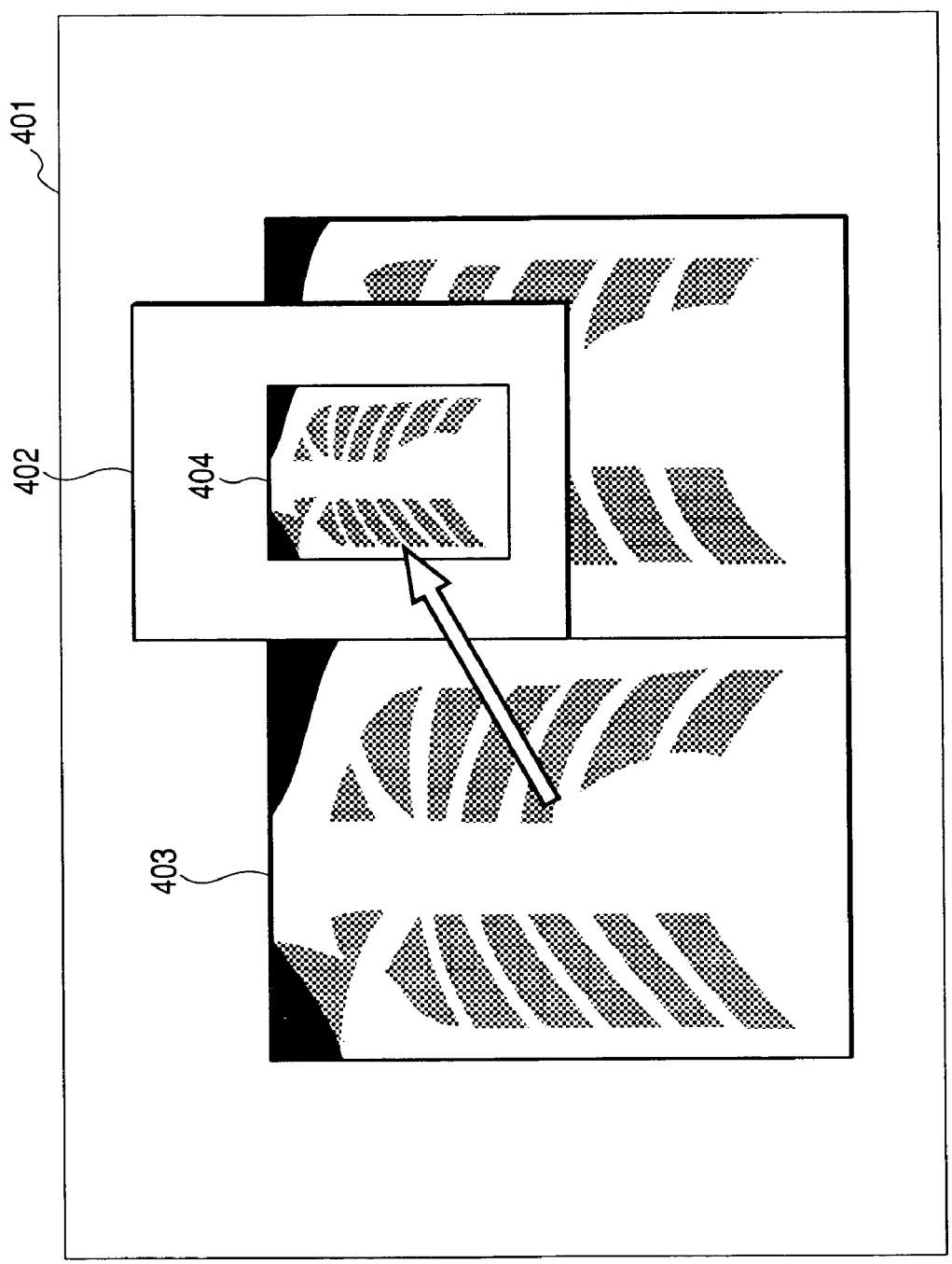
FIG. 3 is a diagram showing an example of an image connection display screen according to the first embodiment of the present invention.

Steps S202, S203 and S204 together are an image selection step of selecting the image to be connected. In the image selection step, as shown in FIG. 3, an image 403 is dragged and dropped by using a mouse from an image display screen 401 to an image connection processing screen 402. In the example shown in FIG. 3, the image 403 displayed on the image display screen 401 is dragged and then dropped on the image connection processing screen 402, whereby an image 404 is displayed as the image to be connected on the image connection processing screen 402. That is, when the image is selected, dragged and dropped on the image connection processing screen 402, the image in question is handled as the image to be subjected to the image connection process. Here, it should be noted that two or more images can be selected, dragged and dropped on the image connection processing screen 402.

When the image to be connected is selected in the step S204, it is possible to adjust the position of the image to be connected, and it is also possible to change the mode. Typically, because the connection position of the image is not adjusted immediately after it was selected, the connection position of the selected image is adjusted.

A step S206 is an image position adjustment step. In this step, after one of the images to be connected is selected, the various processes listed above can be performed on the selected images. More specifically, it is possible to perform upward shift, downward shift, rightward shift and leftward shift of the image so as to adjust the connection position thereof. Moreover, it is possible to perform 90° rotation, −90° rotation, free rotation, up-and-down inversion, front-and-back reversal, density adjustment, cutout and the like of the image. At that time, it is preferable to register the connection positions of the successive images and thus perform the image position adjustment by using upward-shift, downward-shift, rightward-shift and leftward-shift keys on a keyboard, or by selecting (dragging) the image with use of the mouse. Also, when a new image to be connected is dragged and dropped on the image connection processing screen 402, it is possible to add the image to be subjected to the image connection process and thus perform the image position adjustment on the images including the added image. Incidentally, it should be noted that the mentioned free rotation is an image rotation of arbitrary angle.

A step S205 is an operation request selection step. That is, a not-shown changeover button is prepared on the image connection processing screen 402, and the mode is changed by depressing this button. Incidentally, although the mode is changed by depressing the appropriate button in the present embodiment, the present invention is not limited to this. For example, it is contemplated that the mode can be selected on a pull-down menu. Moreover, it is also contemplated that the mode can be changed by depressing, e.g., an appropriate mode changeover key on the keyboard, by double-clicking the mouse, or the like. That is, the mode may be changed through various interfaces. Steps S207 and S208 together are a mode changeover step of changing the image position adjustment mode to the image measurement mode.

Step S207 is an image position adjustment function use inhibition step. In this step, when the mode is changed from the image position adjustment mode to the image measurement mode, the image position adjustment function is set to be unusable, that is, the usable function is changed.

More specifically, in the image measurement mode, the functions for shifting the image upward, downward, rightward and leftward are set to be unusable. In addition, other image adjustment functions are also set to be unusable. As described above, such an unusable state is set as, e.g., a button disable state or a button undisplayed state (the state that a button itself is not displayed so as not to be able to select the function corresponding to the button in question).

Step S208 is an image measurement function use permission step. That is, in this step, the state that the image measurement function cannot be selected is changed through a user interface to the state that the image measurement function can be selected. For example, in a case where a desired function is selected by depressing a corresponding button on the user interface, the state that the button cannot be depressed or clicked is changed to the state that the button can be depressed or clicked. Alternatively, the state that the button itself is not displayed is changed to the state that the button is displayed. Likewise, in a case where a desired function is selected from a pull-down menu, the state that the corresponding item on the menu cannot be selected is changed to the state that the items on the menu can be selected. Alternatively, the state that the function itself is not displayed as the item on the menu is changed to the state that the function is displayed as the item on the menu. More specifically, in the image measurement mode, a function for measuring the distance between two points, a function for measuring an angle, and the like can be used. In addition, a function for measuring lateral curvature by the known Cobb method, a function for measuring the lateral curvature by the known Ferguson method, and other various diagnostic measurement functions can be used.

Incidentally, although the processing in step S208 is performed after the processing in step S207 is performed in the present embodiment, the present invention is not limited to this. That is, the processing in step S207 may be performed after that in step S208.

Step S209 is an operation request judgment step. Thus, when it is judged in step S209 that a request for image measurement is input, the flow advances to step S210 to measure the image. Further, when it is judged in step S209 that a request for image output is input, the flow advances to step S213 to output the image. Moreover, when it is judged in step S209 that a request for mode changeover is input, the flow advances to step S211 to inhibit the image measurement function.

Step S210 is an image measurement step. In this step, it is possible to perform various measurements by using the function for measuring the distance between two points, the function for measuring the angle, the function for measuring the lateral curvature by the Cobb method, the function for measuring the lateral curvature by the Ferguson method, and the like, all described as above, and the measured result is displayed on the connected image. Step S211 is an image measurement function inhibition step.

Step S212 is an image position adjustment function use permission step. That is, in this step, the state that the image position adjustment function cannot be selected is changed through a user interface to the state that the image position adjustment function can be selected. For example, in the case where the desired function is selected by depressing the corresponding button on the user interface, the state that the button cannot be depressed or clicked is changed to the state that the button can be depressed or clicked. Alternatively, the state that the button itself is not displayed is changed to the state that the button is displayed. Incidentally, the mode is changed to the image measurement mode in steps S211 and S212. However, for example, when the connected image is insufficient and thus fine adjustment thereof becomes further necessary, the image measurement mode is again changed to the image position adjustment mode. At that time, the functions capable of being used in the image measurement mode cannot be used, while the functions capable of being used in the image position adjustment mode can be used.

Steps S211 and S212 together are a mode changeover step, as well as steps S207 and S208. In the above steps S207 and S208, the image position adjustment mode is changed to the image measurement mode. Meanwhile, in steps S211 and S212, the image measurement mode is changed to the image position adjustment mode.

Figure 4:
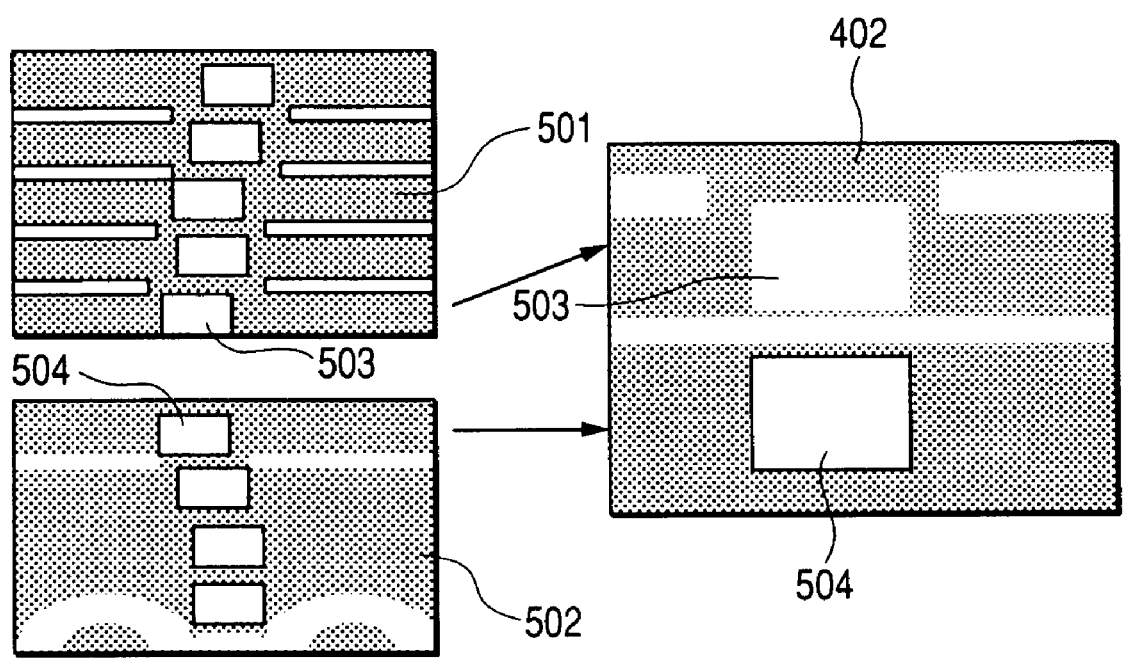
FIG. 4 is a diagram showing an example in which a connection portion of images to be connected is enlarged and displayed, according to the first embodiment of the present invention.

In the image position adjustment mode, as shown in FIG. 4, the connection portion of images 501 and 502 to be connected with each other is enlarged on the image connection processing screen 402 to perform a fine adjustment of the connection position thereof.

In an example shown in FIG. 4, a bone portion 503 of the image 501 and a bone portion 504 of the image 502 are enlarged and displayed, and the positions of these portions are adjusted so that they overlap with each other. When the image position adjustment mode is changed to the image measurement mode in this state, an enlargement/reduction process is performed to the connected image so that it can be displayed within the range of the image connection processing screen 402.

Incidentally, although the processing in step S212 is performed after the processing in step S211 in the present embodiment, the present invention is not limited to this. That is, the processing in step S211 may be performed after that in step S212.

Step S213 is an image output step that the connected image is output. In the present embodiment, it is conceivable that the connected image output in step S213 is stored in an image server, a medical image printer, a local disk or the like. However, the present invention is not limited to this, that is, the output in this step includes whole outputs from the radiographic image connection processing apparatus to the external.

As described above, according to the present embodiment, in the case where the images 501 and 502 are connected with each other, the position adjustment of the images 501 and 502 to be performed by the image position adjustment means 102 (in the image position adjustment mode) and the image measurement to be performed by the image measurement means 104 (in the image measurement mode) are appropriately changed over by the image position adjustment mode/image measurement mode changeover means 103. Thus, only the functions concerning the image position adjustment can be used in the image position adjustment mode, only the functions concerning the image measurement can be used in the image measurement mode, and the image measurement can be performed only after the positions of the images 501 and 502 are determined. For this reason, it is possible to prevent the conventional problem that the connected image at the time of image measurement differs from the connected image to be finally output because the position of the image is changed after this image was measured. Moreover, according to the present embodiment, it is set to be able to use only the functions corresponding to the usable mode, whereby the ease of using the system, as opposed to conventional ones, can be improved.

Second Embodiment

Next, the second embodiment of the present invention will be explained. In the explanation of the present embodiment, the same parts as those in the above first embodiment are denoted by the corresponding numerals and symbols shown in FIGS. 1 to 4 as occasion demands, and the detailed explanation thereof will be omitted.

Figure 5:
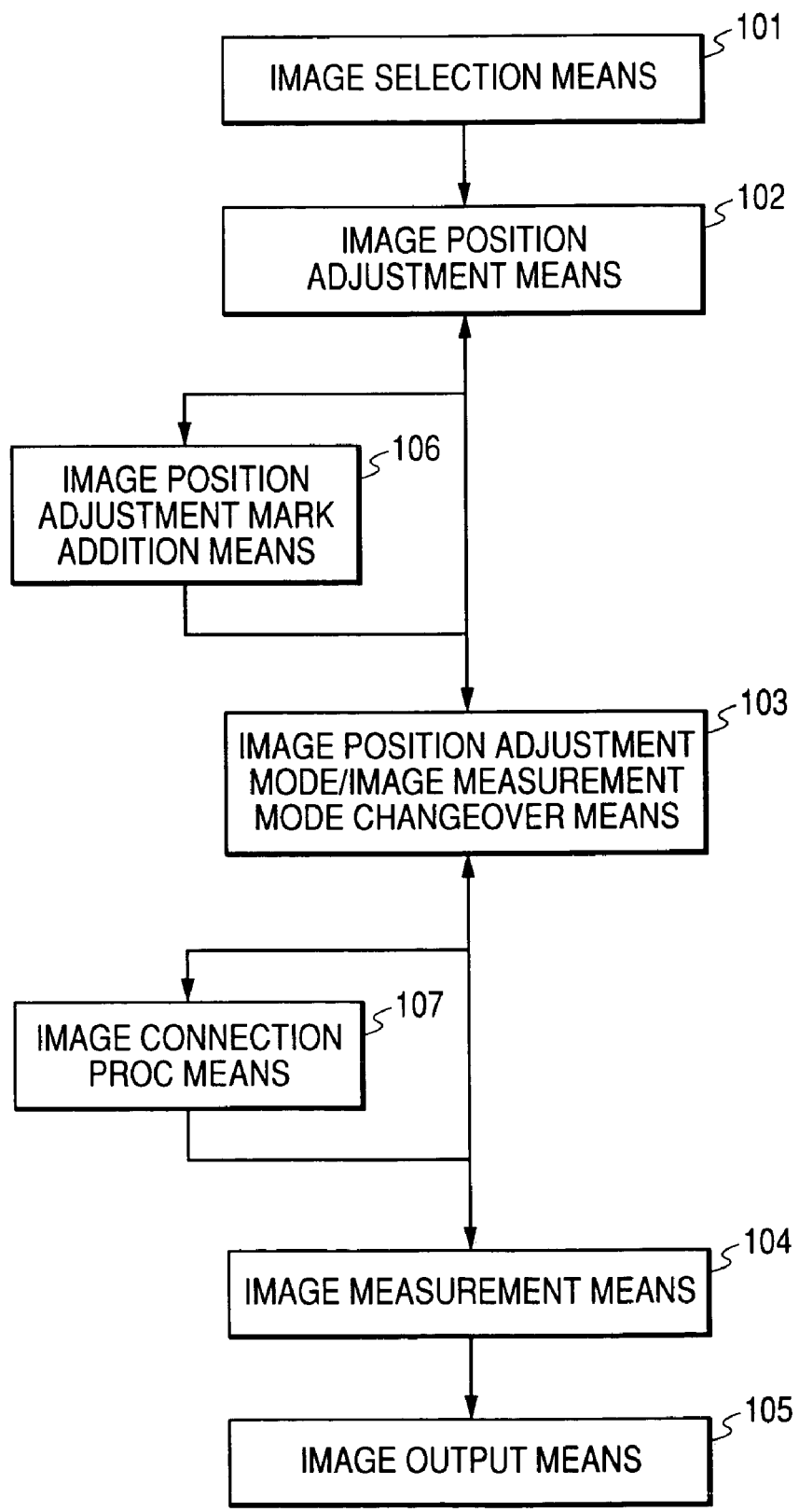
FIG. 5 is a block diagram showing an example of the structure of a radiographic image connection processing apparatus according to the second embodiment of the present invention.

FIG. 5 is a block diagram showing an example of the structure of a radiographic image connection processing apparatus according to the present embodiment.

As shown in FIG. 5, the radiographic image connection processing apparatus in the present embodiment is provided by adding an image position adjustment mark addition means 106 to the radiographic image connection apparatus of the first embodiment shown in FIG. 1. Here, the image position adjustment mark addition means 106 is used to add a mark for performing position adjustment of a connected image, on the image.

Figure 6B:
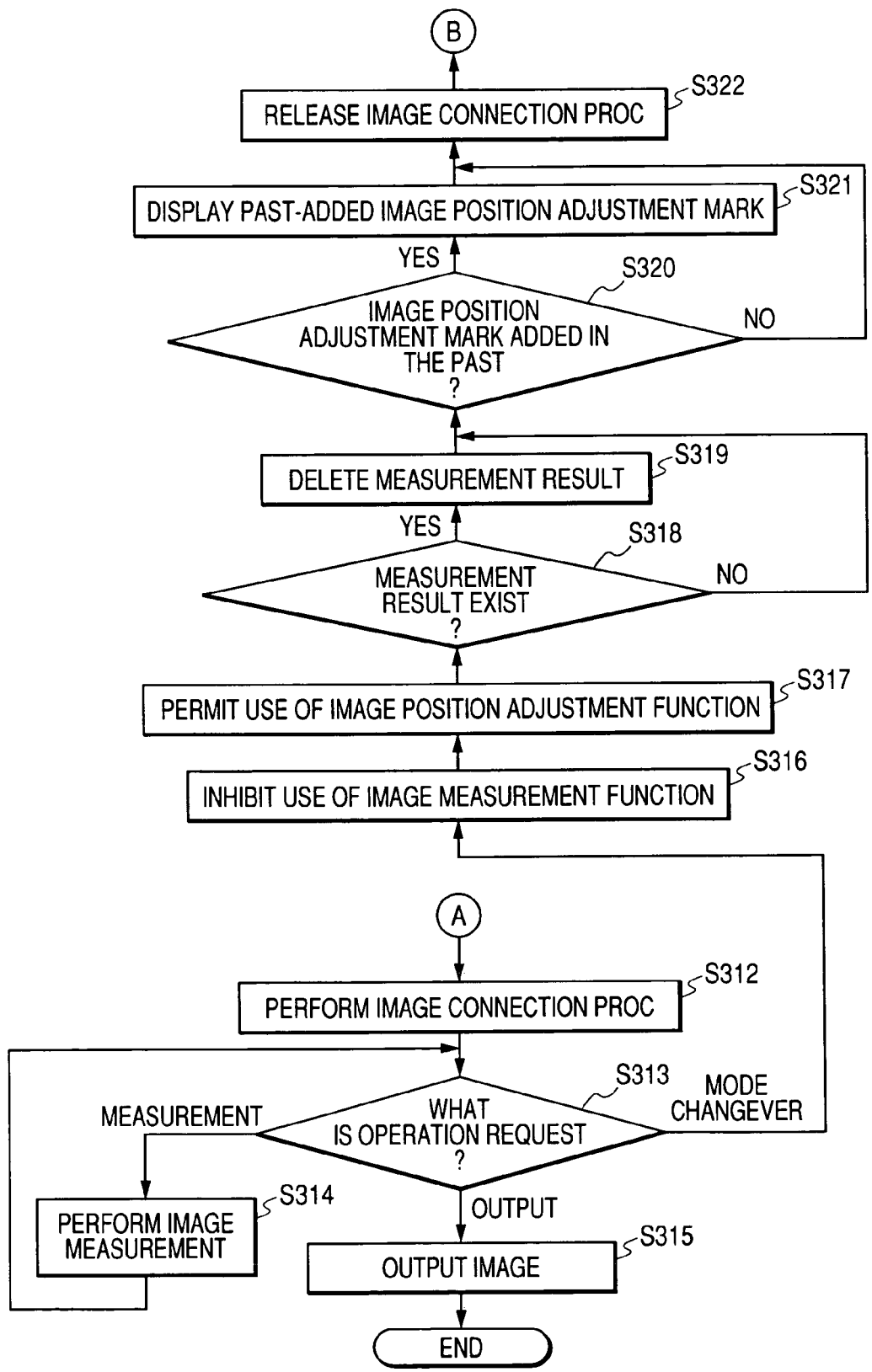
FIG. 6, comprised of FIGS. 6A and 6B, which are flow charts of an example of the operation procedure of the radiographic image connection processing apparatus according to the second embodiment of the present invention.

Next, an example of the operation procedure of the radiographic image connection processing apparatus according to the present embodiment will be explained with reference to the flow charts shown in FIGS. 6A and 6B.

Figure 2:
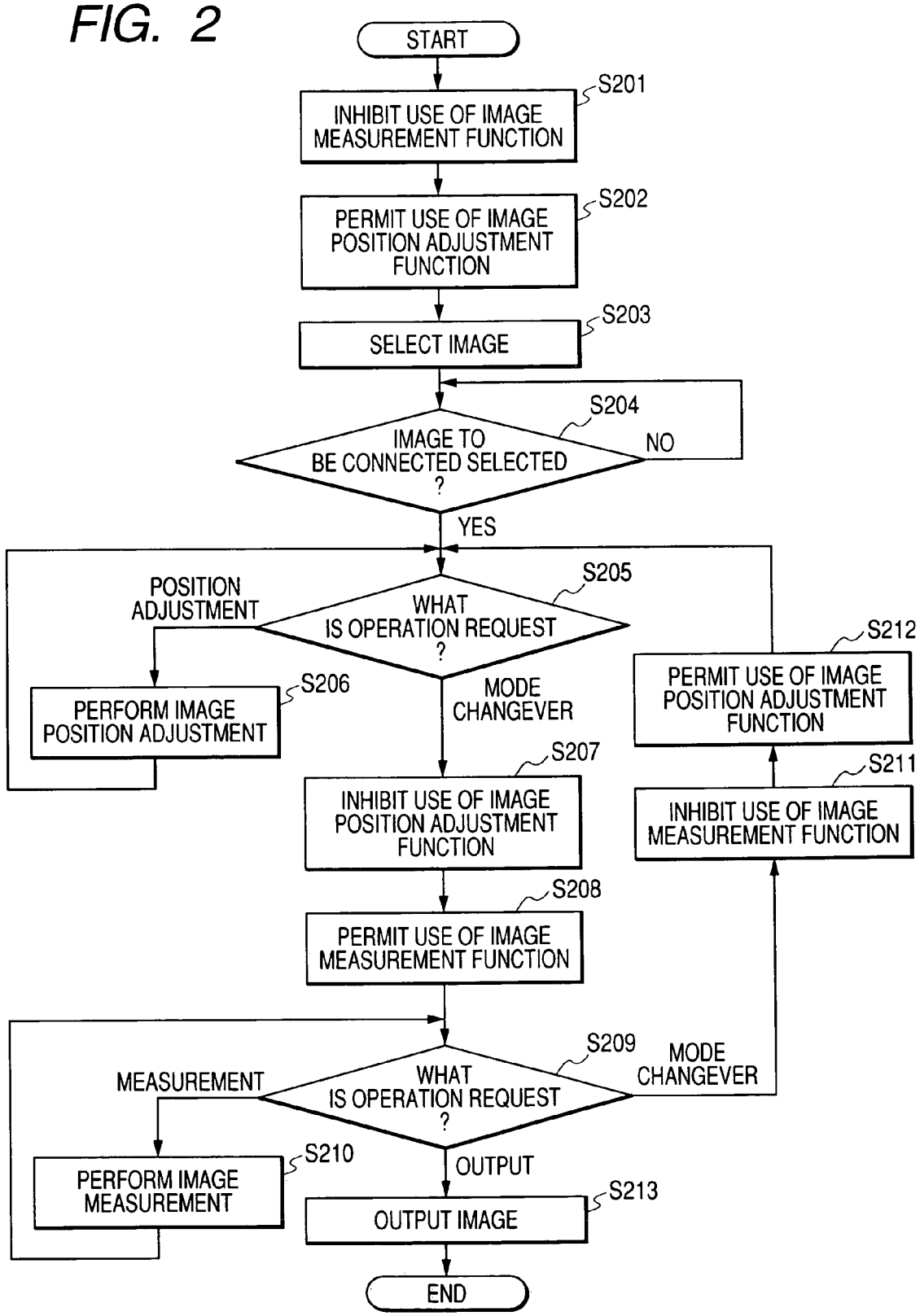
FIG. 2 is a flow chart showing an example of the operation procedure of the radiographic image connection processing apparatus according to the first embodiment of the present invention.

Steps S301 to S306 are respectively the same as steps S201 to S206 of the first embodiment shown in FIG. 2. That is, the S301 is an image measurement function use inhibition step of setting an image measurement function to be unusable. Step S302 is an image position adjustment function use permission step, and steps S303 and S304 together are an image selection step of selecting the image to be connected. Steps S305 and S306 together are a position adjustment step.

Figure 7:
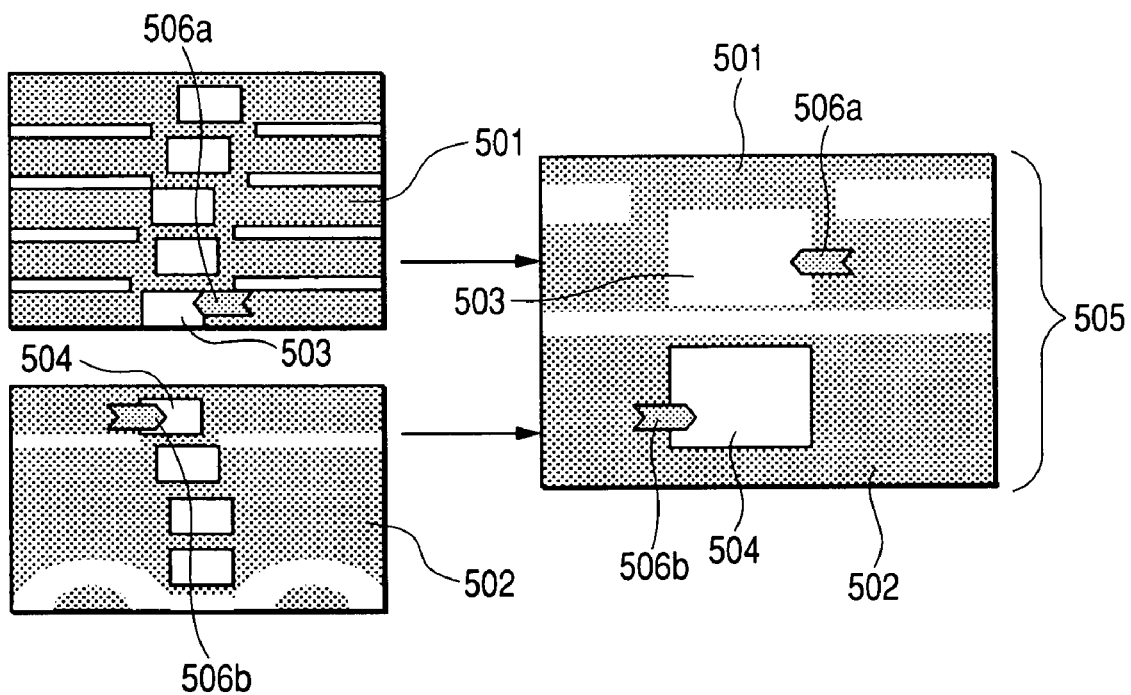
FIG. 7 is a diagram showing an example in which a connection portion of images to be connected is enlarged and displayed, according to the second embodiment of the present invention.

Moreover, step S323 is an image position adjustment mark addition step. That is, as shown in FIG. 7, in an image position adjustment mode, images 501 and 502 are sufficiently enlarged on an image connection processing screen 505, and thus the enlarged images 501 and 502 are handled and processed to finely adjust the connection position. Here, when it is intended to make a fine adjustment of images 501 and 502 in such states as displayed on the image connection processing screen 505, there is a possibility that a user cannot successfully judge which of in-body constituents should be matched (connected), because the user cannot see the whole of the images 501 and 502 on the image connection processing screen 505, the shapes of the in-body constituents are almost similar, and the like.

Therefore, in the present embodiment, before images 501 and 502 are enlarged for the fine adjustment, image position adjustment marks 506a and 506b are added respectively onto the images 501 and 502. Here, it should be noted that the mark is used to indicate which parts on the images should be matched (connected). Thus, even in the case where the images 501 and 502 are sufficiently enlarged for the fine adjustment, it is possible easily to specify the parts to be matched (connected) because the user can do so while checking the marks 506a and 506b (see bone portions 503 and 504 in FIG. 7).

Step S306 is equivalent to step S206 in the first embodiment, that is, step S306 is an image position adjustment step. In this step, after one of the images to be connected is selected, and the connection positions of the selected images are adjusted by performing upward shift, downward shift, rightward shift and leftward shift of the images. Steps S305, S307, S308, S324, S309, S310, S311 S312 are together an image position adjustment mode/image measurement mode changeover step of changing the image position adjustment mode to an image measurement mode through a user interface such as a changeover button or the like. Step S307 is an image position adjustment function use inhibition step of setting the image adjustment function to be unusable.

Steps S324, S309, S310 and S311 are together an image position adjustment mark deletion and image measurement function display step. In the present embodiment, because the image position adjustment mode has been changed to the image measurement mode in step S305, the image position adjustment marks 506a and 506b are released or deleted respectively from the images 501 and 502 in step S309.

It should be noted that, in the present embodiment, it intends to use the image position adjustment marks 506a and 506b for finely adjusting the images 501 and 502 respectively, that is, it is unnecessary to display these marks in the image measurement mode. In addition to the above, there is a fear that the image position adjustment marks 506a and 506b accidentally hide the in-body constituents on the screen from the user while the image measurement is being performed. That is, because the image position adjustment marks 506a and 506b might counteract the image measurement, it is preferable not to display these marks in the image measurement mode. Moreover, it should be noted that, in step S309, the image measurement function is set to be usable.

The step S310 is a past measurement result judgment step of judging whether or not the past measurement result exists. Here, it should be noted that the past measurement result is the result which has been obtained in the image measurement performed in the past. That is, in a case where the image measurement is performed in the image measurement mode past changed from the image position adjustment mode, it is judged in the step S310 whether or not to redisplay the past measurement result on the image. Then, when it is judged in the step S310 that the past measurement result exists, the flow advances to the step S311, while when it is judged in the step S310 that the past measurement result does not exist, the flow advances to the later-described step S312.

The step S311 is a measurement result display step of displaying the measurement result when it is judged in the step S310 that the past measurement result exists. In this step, the past measurement result existing is essentially redisplayed on the image. However, when the image position has been already changed, the measurement result might not be redisplayed. Incidentally, when the measurement result has been concluded in one image before the image connection, the measurement result is redisplayed. Moreover, even when the image position has been already changed, the measurement result is redisplayed if it represents the correct value.

Incidentally, the order of the image position adjustment function use inhibition step of step S307 and the image position adjustment function use permission step of step S308 may be reversed. Moreover, the order of the image position adjustment mark deletion step of steps S324 and S309 and the image measurement result display step of steps S310 and S311 may be reversed.

Step S312 is an image connection processing step. The images to be subjected to the image connection process may include an image of which the image data amount is highly large, for example, there is a case where the image data amount of one image is 15 megabytes (MB) or so. In such a case, when all the image data of the original images are stored and held in a memory and then the image adjustment is performed, it takes a long time for the image process, and a load is very large. For this reason, a reduction image might be generated from the real image data at the time when the image position adjustment is performed, and then the image position adjustment might be performed by using the generated reduction image.

In that case, the real image (that is, the real-size image which is not reduced) is displayed based on the image data of the original image at the timing when the image position adjustment mode is changed to the image measurement mode. However, when a memory having a sufficient capacity is used, or when a high-throughput computer is used, all the necessary processes may be performed based on the image data of the original image. On the contrary, when a memory merely having a poor capacity is used, or when a low-throughput computer is used, the image connection process in step S310 may be performed based on the image data of the reduced image.

As well as step S209 of the first embodiment shown in FIG. 2, step S313 is an operation request judgment step. Thus, when it is judged in step S313 that a request for image measurement is input, the flow advances to step S314 to measure the image. Further, when it is judged in step S313 that a request for image output is input, the flow advances to step S315 to output the image. Moreover, when it is judged in step S312 that a request for mode changeover is input, the flow advances to steps S316 and S317 to perform a mode changeover process.

Step S314 is equivalent to step S210 in the first embodiment shown in FIG. 2, that is, step S314 is an image measurement step of performing the various image measurements with respect to the images 501 and 502.

As well as steps S211 and S212 of the first embodiment shown in FIG. 2, steps S316 and S317 are an image position adjustment mode/image measurement mode changeover step of changing the image measurement mode to the image position adjustment mode. More specifically, step S316 is an image measurement function use inhibition step of setting the image measurement function to be unusable, and step S317 is an image position adjustment function use permission step of permitting use of the image position adjustment function. That is, in the latter step, the state that the image position adjustment function cannot be selected is changed through a user interface to the state that the image position adjustment function can be selected. For example, in the case where the desired function is selected by depressing or clicking the corresponding button on the user interface, the state that the button cannot be depressed or clicked is changed to the state that the button can be depressed or clicked. Alternatively, the state that the button itself is not displayed is changed to the state that the button is displayed.

Steps S318 and S319 are together a measurement result deletion step. More specifically, it is first judged in step S318 whether or not there exists a measurement result measured and obtained in the image measurement mode before it is changed in the image position adjustment mode/image measurement mode changeover step of the steps S316 and S317. When it is judged that such a measurement result in question exists, the flow advances to step S319, while when it is judged that the measurement result in question does not exist, the flow advances to step S320.

In step S319, because the image measurement mode has been changed to the image position adjustment mode, the measurement result is deleted respectively from the images 501 and 502 because the image result might hinder the user from seeing or watching the constitutes in the images 501 and 502 when finely adjusting the positions of the images 501 and 502. Incidentally, when the image position is changed after the image measurement, the physical relationship between the plural partial radiographic images at the time of the measurement and the plural partial radiographic images after they have been connected is changed. More specifically, because the position measured in the image measurement mode has been changed, the measurement value is resultingly different from the connected image, whereby the measurement value is incorrect. Therefore, in the image position adjustment mode for adjusting the positions of the images 501 and 502, the measurement result obtained in the image measurement mode is not displayed even if it exists. However, exceptionally, with respect to a drawing object which has been concluded in one image before the image connection, the position adjustment is not influenced by image enlargement and reduction, whereby it may retain such an object as it is. In that case, when the position adjustment of the image in question is performed, the drawing object moves according to the adjustment.

Figure 8:
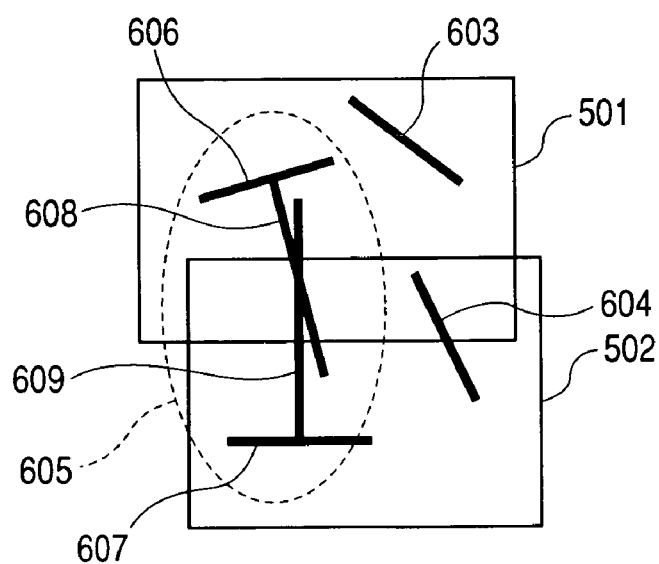
FIG. 8 is a diagram showing an example of a Cobb measured result and a distance measured result according to the second embodiment of the present invention.

However, when the images 501 and 502 are connected with each other and a measurement tool or the like is drawn independently on each of these images as shown in FIG. 8, it might not delete the measurement result. For example, because a distance measurement tool 603 is drawn independently on the image 501, it might not delete this tool. However, in the image position adjustment mode, a case where the measurement tool cannot exist independently might occur by shifting, enlarging and/or reducing the image. In such a case, it is necessary to delete the measurement tool in question.

Moreover, in the measurement method known as the Cobb method, the target to be measured is an image angle. In FIG. 8, numerals 606 and 607 respectively denote auxiliary lines which are in contact with the upper or lower surface of the vertebral bones of spine. Numerals 608 and 609 respectively denote perpendicular lines of the respective auxiliary lines 606 and 607, and the perpendicular lines 608 and 609 are used to measure an angle at the intersection point of the auxiliary lines 606 and 607. Thus, for example, when the relative physical relationship between the auxiliary lines 606 and 607 is maintained by appropriately shifting, enlarging and/or reducing the images 501 and 502, it is unnecessary to delete the auxiliary lines 606 and 607 even when the mode is changed to the image position adjustment mode, and it is possible to shift the auxiliary lines 606 and 607 according to the shifts of the images 501 and 502 (see area 605 in FIG. 8).

On one hand, numerals 603 and 604 denotes an example of tools to be used for measuring the distances. As shown by the distance measurement tool 604 of FIG. 8, when the distance measurement is performed over the plural (here, two) images 501 and 502, it is possible to easily obtain the intended distance between given two points if the enlargement ratio of the image 501 is the same as that of the image 502 and also the pixel pitch of the image 501 is the same as that of the image 502.

However, in a case where the distance of the portion where the images overlap each other is obtained when the enlargement ratio of the image 501 is different from that of the image 502, it is necessary to perform calculation by using the enlargement ratio of either one of the images 501 and 502, by using an intermediate value of the enlargement ratios of both the images 501 and 502, or by changing the enlargement ratio according to a rate of the measurement position.

Besides, in a case where the distance of the portion where the images overlap each other is obtained when the pixel pitch of the image 501 is different from that of the image 502, it is necessary to perform necessary calculation with respect to that portion by using the pixel pitch of either one of the images 501 and 502, or by using an intermediate value of the pixel pitch of both the images 501 and 502.

Incidentally, it might adjust the enlargement ratios of the images 501 and 502 when the images 501 and 502 are enlarged to perform the image adjustment on the enlarged images, or when the images 501 and 502 are enlarged for X-ray photography. Besides, in such cases, it is also possible to consider the enlargements of the images 501 and 502 as the enlargements of the pixel pitches of these images and thus process these images as the images having different pixel pitches. In any case, to cope with the above problem, a limitation that the enlargement ratios of all the images 501 and 502 must be the same might be set in advance when enlarging and/or reducing these images.

Step S320 is a step of judging whether or not the image position adjustment mark exists. That is, in step S320, although the image position adjustment marks 506*a* and 506*b* are not displayed because the currently set mode is the image measurement mode, it is judged whether or not the image position adjustment marks 506*a* and 506*b* have been added in the past. Then, if it is judged that the image position adjustment marks 506*a* and 506*b* have been added, the flow advances to step S321. Meanwhile, if it is judged that image position adjustment marks have not been added, the flow advances to step S322 to release the image connection process.

Step S321 is a step of displaying the past-added image position adjustment marks 506*a* and 506*b* when it is judged in step S320 that the image position adjustment marks 506*a* and 506*b* have been added in the past. That is, the image position adjustment marks 506*a* and 506*b* which have been added in the past are displayed for the fine adjustment operation. Incidentally, in the case where the fine adjustment is performed, when the image position adjustment marks 506*a* and 506*b* respectively added to the different two images 501 and 502 overlap each other, the image position adjustment marks 506*a* and 506*b* may not be displayed. Thus, when the image position adjustment marks 506*a* and 506*b* are not displayed completely, it is possible to consider that the image position adjustment marks 506*a* and 506*b* respectively added to the images 501 and 502 coincide with each other completely.

As described above, according to the present embodiment, the bone portion 503 of the image 501 and the bone portion 504 of the image 502 are enlarged and displayed, and the images 501 and 502 are connected with each other so that these portions overlap each other. In that case, the image position adjustment marks 506*a* and 506*b* are displayed respectively at the bone portions 503 and 504 by the image position adjustment mark addition means 106. Therefore, in addition to the above effects obtained in the first embodiment, it is further possible to prevent that the user cannot judge which portions on the images 501 and 502 he should overlap when the connection portion of the images 501 and 502 is enlarged and displayed, thereby enabling to improve accuracy in the image position adjustment.

More specifically, the connection portion of the images 501 and 502 is sufficiently enlarged to the extent that the whole image cannot be held within the range of the monitor screen, and then the positions of the images 501 and 502 are finely adjusted. In that case, because the images 501 and 502 intended to be connected are sufficiently large with respect to the image frame, the user tends to be unable to judge which portions of the images 501 and 502 should be connected with each other. In particular, when the spine portions on the respective images 501 and 502 are connected with each other, the user tends to be unable to clearly judge which bones in the spine portions should be connected with each other. For this reason, according to the present embodiment, the image position adjustment marks 506*a* and 506*b* are previously added respectively to the spine portions to be connected, the marked portions are sufficiently enlarged, and then the positions of the images 501 and 502 are finely adjusted by accurately connecting these marked portions, thereby improving accuracy in the position adjustment of the images 501 and 502.

Moreover, because the distance measurement tools 603 and 604, the auxiliary lines 606 and 607, and the perpendicular lines 608 and 609 which all concern the measurement result in the image measurement mode are not displayed in the image position adjustment mode, these tools and lines do not counteract the position adjustment of the images 501 and 502 in the image position adjustment mode, whereby it is possible to significantly improve usability in finely adjusting the positions of the images 501 and 502. Moreover, because the image position adjustment marks 506a and 506b or the like are not displayed in the image measurement mode, these marks do not counteract the image measurement operation in the image measurement mode. In addition, because the image position adjustment marks 506a and 506b added in the past are remained, these remaining marks can be added when the mode is again changed from the image measurement mode to the image position adjustment mode, whereby it is unnecessary to again add the past-added image position adjustment marks 506a and 506b.

Incidentally, when the positions of the images 501 and 502 are adjusted, the image adjustment is performed with respect to the reduction image obtained by reducing the real image, and the image which has been subjected to the same image connection process as that for the connection image to be actually output is displayed after the position adjustment, whereby it is possible to reduce a time period necessary for adjusting the positions of the images 501 and 502. Thus, it is possible to achieve high-throughput interactive position adjustment. On one hand, after the position adjustment of the images 501 and 502 ended, the image connection process is performed with respect to the image to be actually output, whereby it is possible for the user to see or watch the image equivalent to the image to be finally output. Thus, it is possible for the user to confirm the output image then and there, and it is also possible to achieve high-accuracy image measurement. Moreover, the connection image is displayed so as to be exactly held within the image frame being displayed in the case where the mode is changed to the image measurement mode, whereby it is possible for the user to easily confirm the whole image.

In addition, when the image position adjustment marks 506a and 506b respectively added to the images 501 and 502 being the target of the image connection mutually overlap, the image position adjustment marks 506a and 506b are not displayed, whereby the user can know that the images 501 and 502 intended to be connected exactly coincide with each other, on the basis of the fact that the marks 506a and 506b are not displayed. Thus, it is possible to improve usability in the image position adjustment. Moreover, the image position adjustment marks 506a and 506b which overlap with each other are set to be not displayed, whereby there is no obstacle of preventing the user from seeing and watching the actual image. Thus, it is possible for the user to more easily judge whether or not the position adjustment succeeded.

Moreover, in the present embodiment, the images 501 and 502 intended to be connected are enlarged or reduced. Therefore, even when the enlargement ratio of the image 501 is different from that of the image 502, it is possible to adjust the enlargement ratios of both the images 501 and 502 and appropriately connect them with each other. Moreover, when there is no influence due to the image position adjustment, it is possible to display the measurement result as it is. In addition, even when the value of the measurement result extends over the plural pixels of which the enlargement ratios or the pixel pitches are different mutually, it is possible to appropriately perform the image measurement.

OTHER EMBODIMENTS

Figure 9:
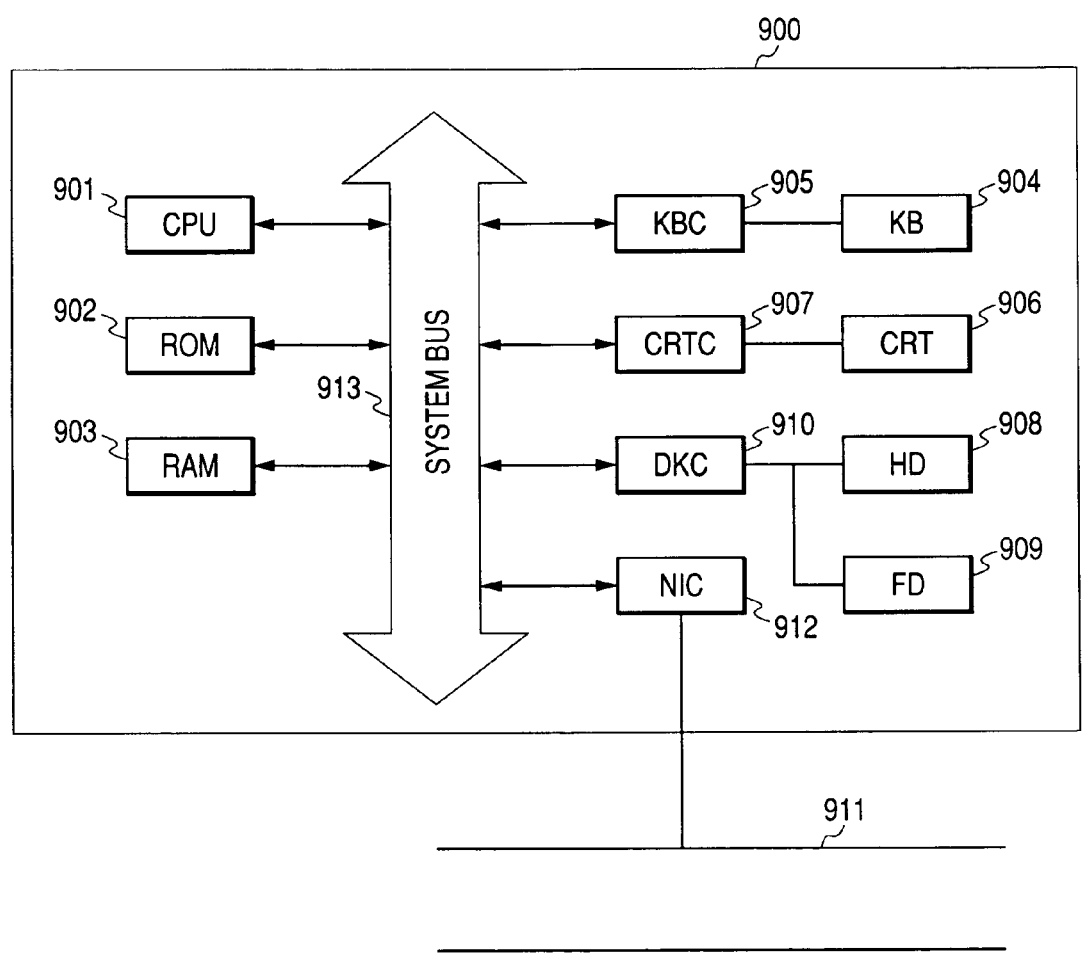
FIG. 9 is a block diagram showing an example of the structure of a computer system disposed in a radiographic image connection processing apparatus according to other embodiments of the present invention.

The control operations of the radiographic image connection processing apparatuses in the above embodiments can be achieved by using a computer system (hardware) as shown in FIG. 9.

FIG. 9 is a block diagram showing an example of the structure of the computer system disposed in the radiographic image connection processing apparatus.

In a computer system 900 shown in FIG. 9, a CPU 901, a ROM 902, a RAM 903, a KBC (keyboard controller) 905 of a KB (keyboard) 904, a CRTC (CRT controller) 907 of a CRT 906 acting as a display unit, a DKC (disk controller) 910 of an HD (hard disk) 908 and an FD (flexible disk) 909, and an NIC (network interface controller) 912 for connecting with a network 911 are appropriately connected together through a system bus 913 in such a manner as capable of communicating mutually.

The CPU 901 executes the software stored in the ROM 902 or the HD 908 or the software supplied from the FD 909, and thus, based on the software, totally controls the structural components respectively connected with the system bus 913.

That is, the CPU 901 reads a processing program according to a predetermined processing sequence from the ROM 902, the HD 908 or the FD 909, and executes the read processing program so as to perform the control for achieving the following operations.

The RAM 903 functions as a main memory of the CPU 901, a working area or the like.

The KBC 905 controls various instructions input from the KB 904, a pointing device (not shown), and the like.

The CRTC 907 controls the display operation by the CRT 906.

The DKC 910 controls accesses to the HD 908 and the FD 909 which store boot programs, various application programs, editing files, user files, network administration programs, predetermined processing programs in the embodiments of the present invention, and the like.

The NIC 912 exchanges various data bi-directionally to/from devices and systems on the network 911.

Incidentally, the present invention includes a case where the object of the present invention can be achieved by supplying program codes of software to achieve the functions of the above embodiments to a computer in a system or an apparatus connected to the various devices and thus operating the various devices according to the programs supplied and stored in the computer (or CPU or MPU) of the system or the apparatus so as to achieve the functions of the above embodiments.

In that case, the program codes themselves of the software achieve the functions of the above embodiments. Therefore, the program codes themselves, and a means for supplying the program codes to the computer, for example, a recording medium storing these program codes, constitute the present invention. As the recording medium of storing the program codes, e.g., a flexible disk, a hard disk, an optical disk, a magneto-optical disk, a CD-ROM, a CD-R, a magnetic tape, a non-volatile memory card, a ROM and the like can be used.

Moreover, it can be obviously understood that the present invention includes not only a case where the functions of the above embodiments are achieved by executing the supplied program codes with the computer, but also a case where an OS (operating system) or the like running on the computer or cooperating with other application software performs a part or all of the actual processes based on instructions of the program codes and thus the functions of the above embodiments are realized by such the processes.

Furthermore, it can be obviously understood that the present invention also includes a case where, after the supplied program codes are written into a function expansion board inserted in the computer or a memory in a function expansion unit connected to the computer, a CPU or the like provided in the function expansion board or the function expansion unit performs a part or all of the actual processes on the basis of the instructions of the program codes, and thus the functions of the above embodiments are realized by such the processes.

As many apparently widely different embodiments of the present invention can be made without departing from the spirit and scope thereof, it is to be understood that the present invention is not limited to the specific embodiments thereof expect as defined in the appended claims.

This application claims priority from Japanese patent Application No. 2003-310438 filed Sep. 2, 2003, which is hereby incorporated by reference herein.

What is claimed is:

1. A method of controlling a radiographic image connection apparatus connecting plural partial radiographic images and measuring a distance, said method comprising:
    a) an image selection step, performed by a processor, of selecting the plural partial radiographic images;
    b) a mode switching step, performed by a processor, of switching between an image position adjustment mode and an image measurement mode;
    c) an image connection processing step, performed by a processor, of connecting the selected partial radiographic images, adding markers indicating which parts on the selected partial radiographic images should be matched on the selected partial radiographic images to be connected;
    d) an image measurement step, performed by a processor, of measuring a distance in the plural partial radiographic images, in the image measurement mode;
    e) a first display control step, performed by a processor, of displaying an object representing the measured distance in the image measurement step and deleting the display of the markers added in the image connection processing step, while in the image measurement mode; and
    f) a second display control step, performed by a processor, of displaying the markers and deleting the display of all of the object added in the image measurement mode, except for the object being independently on one of the selected partial radiographic images, and displaying an enlarged connection portion of the selected partial radiographic images and deleting the markers when the markers overlap each other, while in the image position adjustment mode.

2. A method according to claim 1, further comprising a measurement inhibition step of inhibiting the measurement in a case where the mode has been switched to the image position adjustment mode in said mode switching step.

3. A method according to claim 1, further comprising a position adjustment inhibition step of inhibiting the position adjustment of the partial radiographic image in a case where the mode has been switched to the image measurement mode in said mode switching step.

4. A method according to claim 1, further comprising:
    an image output control step of controlling output of the partial radiographic images connected in said image connection processing step; and
    an image output inhibition step of controlling to inhibit the output of the connected partial radiographic images in the image position adjustment mode.

5. A method according to claim 1, wherein said image connection processing step is executed to connect the partial radiographic images so that one of the partial radiographic images to be connected overlap the other of the partial radiographic images.

6. A radiographic image processing apparatus comprising:
    a) an image selection unit adapted to select the partial radiographic images to be connected;
    b) a mode switching unit adapted to switch between an image position adjustment mode and an image measurement mode;
    c) an image connection processing unit adapted to connect the selected partial radiographic images, adding markers indicating which parts on the selected partial radiographic images should be matched on the selected partial radiographic images to be connected;
    d) an image measurement unit adapted to measure a distance in the plural partial radiographic images, in the image measurement mode;
    e) a first display control unit adapted to display an object representing the measured distance the image measurement unit and to delete the display of the markers added by the image connection processing unit, while in the image measurement mode; and
    f) a second display control unit adapted to display the markers and to delete the display of all of the object added in the image measurement mode, except for the object being independently on one of the selected partial radiographic images, and to display an enlarged connection portion of the selected partial radiographic images and deleting the markers when the markers overlap each other, while in the image position adjustment mode.

7. A apparatus according to claim 6, further comprising an image measurement unit adapted to measure the partial radiographic images selected by said image selection unit,
    wherein said image measurement unit inhibits the measurement in a case where the mode has been switched to the image position adjustment mode by said mode switching unit.

8. A apparatus according to claim 6, further comprising an image position adjustment unit adapted to adjust a position of the partial radiographic image selected by said image selection unit,
    wherein said image position adjustment unit inhibits the position adjustment in a case where the mode has been switched to the image measurement mode by said mode switching unit.

9. A apparatus according to claim 6, further comprising an image output control unit adapted to control output of the partial radiographic images connected by said image connection processing unit,
    wherein said output control unit controls to inhibit the output of the connected partial radiographic images in the image position adjustment mode.

10. A apparatus according to claim 6, wherein said image connection processing unit connects the partial radiographic images so that one of the partial radiographic images to be connected overlap the other of the partial radiographic images.

11. A computer-readable recording medium, storing a computer program, in executable form, for causing a computer to perform a method of controlling a radiographic image connection apparatus for connecting plural partial radiographic images and measuring a distance, said method comprising:

a) an image selection step of selecting the plural partial radiographic images;
b) a mode switching step of switching between an image position adjustment mode and an image measurement mode;
c) an image connection processing step of connecting the selected partial radiographic images, adding markers indicating which parts on the selected partial radiographic images should be matched on the selected partial radiographic images to be connected;
d) an image measurement step of measuring a distance in the plural partial radiographic images, in the image measurement mode;
e) a first display control step of displaying an object representing the measured distance in the image measurement step and deleting the display of the markers added in the image connection processing step, while in the image measurement mode; and
f) a second display control step of displaying the markers and deleting the display of all of the object added in the image measurement mode, except for the object being independently on one of the selected partial radiographic images, and displaying an enlarged connection portion of the selected partial radiographic images and deleting the markers when the markers overlap each other, while in the image position adjustment mode.

* * * * *